United States Patent [19]

Kobayashi et al.

[11] 4,101,651

[45] Jul. 18, 1978

[54] PROCESS FOR PREPARING PREPARATIONS FOR ORAL ADMINISTRATION

[75] Inventors: Toshiyuki Kobayashi, Yokohama; Akio Okada, Kawasaki; Takeshi Mayama, Chigasaki; Akira Okada, Zushi, all of Japan

[73] Assignee: Meiji Seika Kaisha, Ltd., Tokyo, Japan

[21] Appl. No.: 655,026

[22] Filed: Feb. 3, 1976

[30] Foreign Application Priority Data

Sep. 29, 1975 [JP] Japan .................. 50-117513

[51] Int. Cl.$^2$ ................ A61K 9/16; A61K 31/74; A61K 31/78
[52] U.S. Cl. ........................ 424/35; 424/78; 424/81
[58] Field of Search .................. 424/10, 35, 78

[56] References Cited

U.S. PATENT DOCUMENTS

| | | | |
|---|---|---|---|
| 3,242,049 | 3/1966 | O'Brien et al. | 424/35 |
| 3,247,065 | 4/1966 | Koff | 424/35 |
| 3,859,228 | 1/1975 | Morishita et al. | 424/35 |
| 3,860,733 | 1/1975 | Morse et al. | 424/35 |
| 3,879,511 | 4/1975 | Goodhart et al. | 424/35 |
| 3,891,570 | 6/1975 | Fukushima et al. | 424/35 |
| 3,906,086 | 9/1975 | Guy et al. | 424/35 |

FOREIGN PATENT DOCUMENTS

| | | | |
|---|---|---|---|
| 908,282 | 10/1962 | United Kingdom | 424/35 |
| 1,033,684 | 6/1966 | United Kingdom | 424/35 |

OTHER PUBLICATIONS

Remington's Practice of Pharmacy, 13th Ed. (1965), Mack Pub. Co., Easton, Pa., p. 559.

Martin–Husa's Pharmaceutical Dispensing, (1966), Mack Pub. Co., Easton, Pa., pp. 67–73 & 109–111.

*Primary Examiner*—Frederick E. Waddell
*Attorney, Agent, or Firm*—Sughrue, Rothwell, Mion, Zinn and Macpeak

[57] ABSTRACT

A process for preparing preparations for oral administration which do not have a bitter taste which comprises either dissolving a bitter taste-masking substance at a high concentration in a solvent to be used for dissolving or suspending a bitter active ingredient and adding the active ingredient to the resulting solution followed by kneading, or kneading a solution or suspension in which a bitter active ingredient has been dissolved or suspended with the bitter taste-masking substance, adding silicic acid anhydride to the resulting kneaded substance to form a powder and granulating the powder using a solution of the bitter taste-masking substance in a fluidized bed granulator.

4 Claims, No Drawings

PROCESS FOR PREPARING PREPARATIONS FOR ORAL ADMINISTRATION

BACKGROUND OF THE INVENTION

1. Field of the Invention

This invention relates to a process for preparing preparations for oral administration (hereinafter, referred to as oral preparations for brevity), more particularly, to a process for masking the bitter taste of an active ingredient which tastes bitter when administered orally.

2. Description of the Prior Art

In general, many pharmaceuticals have an unpleasant taste, particularly they have a bitter taste or create an irritating sensation upon oral administration. Such pharmaceuticals include many important ones, for example, antibiotics such as macrolide antibiotics, e.g., midecamycin, kitasamycin, josamycin, erythromycin, etc., tetracyclic antibiotics, chloramphenicol and the like, synthetic pharmaceuticals such as chlorpromazine hydrochloride, ethaphenon hydrochloride, buformin hydrochloride, etc., and many other pharmaceutical agents.

The inventors have conducted extensive research on processes for making such bitter active ingredients easy to take orally, and previously completed the inventions described in their copending Japanese Patent Applications 80179/1974 and 80180/1974.

As a result of further research, the inventors reached the present invention in which there is provided a method for masking the bitter taste of macrolide antibiotics such as midecamycin, kitasamycin, josamycin and the like.

SUMMARY OF THE INVENTION

The present invention provides a process for preparing oral preparations which have no bitter taste, which process comprises either dissolving a bitter taste-masking substance at a high concentration in a solvent to be used for dissolving or suspending a bitter active ingredient and adding the active ingredient to the resulting solution followed by kneading, or kneading a solution or suspension in which the bitter active ingredient has been dissolved or suspended with the bitter taste-masking substance, adding silicic acid anhydride to the resulting kneaded substance to form a powder and granulating the powder using a solution of the bitter taste-masking substance in a fluidized bed granulator.

Both processes are essentially composed of the following two steps: (1) kneading one or more a bitter active ingredient with one or more bitter taste-masking substances and silicic acid anhydride to form a powder (kneaded substance); and (2) granulating the powder using a solution of one or more bitter taste-masking substances in a fluidized bed granulator.

DETAILED DESCRIPTION OF THE INVENTION

The present invention differs from either of the inventors described in the above cited Japanese Patent Applications which had previously been proposed in that a bitter active ingredient and a bitter taste-masking substance are once dissolved in a solvent.

According to the present invention, in preparing oral preparations from the above described active ingredients a bitter taste-masking substance is dissolved at high concentration in a solvent (the solvent is used in an amount the same as or more than the weight of the active ingredient) for the active ingredient, and then the active ingredient is added thereto followed by thoroughly kneading.

Alternatively, the bitter active ingredient is first dissolved or suspended in a solvent (the solvent is used in an amount the same as or more than the weight of the active ingredient for the bitter taste-masking substance, and the bitter taste-masking substance is then added thereto followed by thoroughly kneading. Thereafter, silicic acid anhydride is added to the resulting kneaded substance to pulverize the same, and the powder thus formed is crushed and dried.

By the above-mentioned procedures, it is possible to mask about 50% of the bitter taste. The remaining bitter taste can be masked by granulating the above powder obtained by mixing (kneading) the bitter taste active ingredient with a bitter taste-masking substance and silicic acid anhydride using a bitter taste-masking substance by means of a fluidized bed granulator, thereby obtaining a powdered preparation free of bitter taste.

The present invention thus provides a process for preparing an oral preparation which comprises a combination of a treatment in which a bitter taste-masking substance and a bitter active ingredient are kneaded while in the dissolved state and a treatment in which the above kneaded substance is granulated with a bitter taste-masking substance using a fluidized bed granulator, thereby masking the bitter taste completely. In order to flavor the thus prepared preparations, if desired, a blend of appropriate flavoring agents such as sucrose, mannitol, saccharin, citric acid, common salt and the like can be granulated and then mixed with the above powdered preparation to obtain a granulated preparation which has a further improved taste and which is easy to take, even for infants. The amount of the flavoring agent added is not overly important, and can easily be determined by one skilled in the art, i.e., one or more flavoring agents are added in an amount sufficient to impart an effective degree of the flavor of the flavoring agent to the composition.

The compositions of the present invention are, of course, orally administered, and they are typically administered so as to provide an amount of active ingredient therein which is in accordance with conventional doses for the active ingredient. In this regard, no invention is attached to the amount of active ingredient administered since such is in accordance with standard pharmaceutical/medical techniques, and the diseases or conditions treatable depend upon the active ingredient utilized (bitter active ingredient) and are also entirely in accordance with conventional pharmaceutical/medical techniques. They are particularly useful for the treatment of infections caused by gram positive and negative bacteria or for the treatment of diabetes mellitus.

The bitter taste-masking substances which can be used in this invention include water-insoluble high molecular weight substances as are commonly employed in pharmaceutical preparations, for example, one or more of ethyl cellulose, hydroxypropylmethyl cellulose phthalate, cellulose acetate phthalate, polyvinyl acetal diethylaminoacetate, dimethylaminoethyl methacrylate-methyl methacrylate copolymers, methylvinylpyridine methylacrylate-methacrylate copolymers and the like. Preferred bitter taste-masking substances have a molecular weight more than about 2,000.

The solvent or solvents used in the practice of the present invention are not overly important so long as the solvent is volatile and does not exert any degrading effect upon the constituents of the composition of the present invention. The reason that the solvent(s) used is not overly important is, of course, that the solvent is removed from the final product of the present invention. Typical solvents are haloalkanes such as methyl chloride or 1,1,1-trichloroethane.

One or more of the above-described bitter taste-masking substances to be kneaded with one or more bitter active ingredients are sufficiently used in an amount of about 0.5 to about 3 times, preferably 0.5 to 2 times, the weight of one or more active ingredients, and the amount used for granulation is sufficient in an amount of about 1/10 to about 1/5 the above-recited range. The amount of the silicic acid anhydride is not particularly limited, but pulverization is sufficiently effected using the same in an amount equal to or less than the bitter taste-masking substance used.

The temperature and pressure of operation of the process of the present invention are not overly important, so long as none of the materials involved are degraded during processing and, of course, so long as the solvent(s) used can be volatilized. Typically, processing is at atmospheric pressure but nothing would prohibit the use of sub- or super-atmospheric pressures, though correspondingly there would be no substantial benefits in product quality or ease of operation obtained. At the same time, processing is typically at room temperature, though in a fashion similar to the pressure of operation nothing would prevent operation at lower or higher temperatures, though again there is no commensurate increase in product quality.

Balancing all factors in ease of operation, seldom will operation be at other than atmospheric pressure and at room temperature.

The present invention will now be illustrated in greater detail by way of several Examples, but it should be understood that they are given for illustrative purposes only and are not to be construed as limiting the invention. In the Examples, all parts, percentages, ratios and the like are by weight and all processings at room temperature and atmospheric pressure, unless otherwise indicated.

EXAMPLE 1

1 kg of ethyl cellulose was added to a solution of 1 kg of midecamycin dissolved in 2 liters of methylene chloride, and the resulting mixture was thoroughly kneaded using a mixer for about 30 minutes. 0.9 kg of silicic acid anhydride was then added to the kneaded substance followed by kneading to pulverize the mixture and yield a powder. The resulting powder was dried at 50° C for 3 hours. The powder was then granulated using a 2% 1,1,1-trichloroethane solution of 160 g of ethyl cellulose (National formulary XIII) by means of a fluidized bed granulator for about one hour to obtain a granulated active ingredient having the bitter taste thereof masked. On the other hand, a mixture of 10 kg of mannitol and 30 g of sodium saccharin was granulated in a conventional manner using a 2% aqueous solution of hydroxypropyl cellulose to obtain granules for flavoring. The above granulated active ingredient and flavoring granules and a trace amount of a flavoring agent were mixed in such proportions that 100 mg of midecamycin was contained per g of the resulting mixture to obtain fine granules (< 250 μ) of midecamycin (sample A) which did not have a bitter taste and which were easy to take.

For comparison, 1 kg of midecamycin, 30 g of sodium saccharin, a trace amount of the flavoring agent and mannitol were mixed to make 10 kg. The resulting mixture was granulated using a 2% aqueous solution of hydroxypropyl cellulose by means of a fluidized bed granulator to prepare fine granules containing 100 mg of midecamycin per g (sample B). Taking into consideration tasting tests, samples A and B were assigned to 20 panel members, and a comparative organoleptic test conducted by a two point tasting test method in a manner conventionally employed. The results obtained are shown in Table 1 below.

TABLE 1

| Sample | Bitter | Not Bitter |
| --- | --- | --- |
| A | 0 | 20 |
| B | 20 | 0 |

The results in Table 1 above clearly show that the fine granules of midecamycin obtained according to the present invention do not taste bitter and are easy to take.

EXAMPLE 2

A solution of 1 kg of ethyl cellulose dissolved in 2 liters of methylene chloride was added to 1 kg of midecamycin, and the resulting mixture was thoroughly kneaded for about 1 hour. 0.9 kg of silicic acid anhydride was then added to the kneaded substance followed by mixing to pulverize the same. The resulting powder was dried at 50° C for 3 hours and then worked up in the same manner as described in Example 1 to obtain fine granules of midecamycin which did not have a bitter taste and were easy to take.

EXAMPLE 3

A solution of 1 kg of a dimethylaminoethyl methacrylate-methyl methacrylate copolymer dissolved in 1.5 liters of methylene chloride was added to 1 kg of midecamycin followed by thoroughly kneading for about 1 hour. 1 kg of silicic acid anhydride was then added to the kneaded substance, and the mixture was kneaded to make powders, which were then dried at 40° C for 3 hours. The resulting powder was granulated using a 2% 1,1,1-trichloroethane solution of 200 g of ethyl cellulose by means of a fluidized bed granulator. The granules were worked up in the same manner as described in Example 1 to obtain fine granules of midecamycin which were not bitter and easy to take.

EXAMPLE 4

In the same manner as described in Example 1 but using 1 kg of josamycin, fine granules of josamycin containing 100 mg of the active ingredient per g of the granules which were not bitter and easy to take were prepared.

EXAMPLE 5

In the same manner as described in Example 1 but using 1 kg of kitasamycin, fine granules containing 100 mg of kitasamycin per g of the granules which were not bitter and easy to take were prepared.

EXAMPLE 6

3 kg of ethyl cellulose was dissolved in 28 liters of 1,1,1-trichloroethane, and 1 kg of buformin hydrochloride was added thereto. The mixture was thoroughly kneaded using a mixer to uniformly disperse the buformin hydrochloride. The resulting dispersion was slowly added to synthetic aluminum silicate, and the mixture was kneaded with stirring to form powders, which were then dried at 50° C under reduced pressure for 3 hours followed by grinding. The resulting powder was granulated using a 2% 1,1,1-trichloroethane solution of ethyl cellulose by means of a fluidized bed granulator for about 1 hour. On the other hand, 6 kg of mannitol, 60 g of saccharin and 60 g of common salt were mixed, and the resulting mixture granulated using a 2% aqueous solution of hydroxypropyl cellulose.

The above obtained granules of the active ingredient and the flavoring granules were mixed to obtain granules of buformin hydrochloride which tasted good, i.e., which had no bitter taste, and which were stable.

EXAMPLE 7

1 kg of chloramphenicol was suspended in a solution of 50 g of sorbitan sesquioleate dissolved in 10 liters of methylene chloride, and 2.22 kg of ethyl cellulose was added thereto followed by thoroughly kneading. 2 kg of silicic acid anhydride was added to the kneaded substance to form a powder, which was then dried at 60° C for 3 hours. The powder was granulated using a 2% 1,1,1-trichloroethane solution of ethyl cellulose and a fluidized bed granulator. On the other hand, 10 kg of mannitol, 100 g of saccharin and 100 g of common salt were mixed, and the resulting mixture was granulated in a conventional manner using a 2% isopropyl alcohol solution of hydroxypropyl cellulose to prepare flavoring granules.

The above obtained granules of the active ingredient and the flavoring granules were mixed in a mixing ratio of 6 to 4 by weight to obtain a chloramphenicol preparation (granules) which tasted good and which were stable.

EXAMPLE 8

3 kg of hydroxypropylmethyl cellulose phthalate and 2 g of polyoxyethylene sorbitan monooleate were suspended or dissolved in 5 liters of water, and a 0.1N solution of sodium hydroxide was added thereto followed by stirring to form a solution while maintaining the pH at 7.0. To the resulting solution was added 1 kg of midecamycin as an active ingredient, and the mixture was kneaded with stirring to thoroughly disperse the midecamycin. 4 kg of silicic acid anhydride was then added to the dispersion. The mixture was thoroughly kneaded, dried at 60° C under reduced pressure for 3 hours and then worked up in the same manner as described in Example 6, thereby obtaining granules of midecamycin which had no bitter taste and which were stable.

While the invention has been described in detail and with reference to specific embodiments thereof, it will be apparent to one skilled in the art that various changes and modifications can be made therein without departing from the spirit and scope thereof.

What is claimed is:

1. A process for preparing granular preparations for oral administration having no bitter taste which comprises dissolving a pharmaceutically acceptable water insoluble ethyl cellulose as a bitter taste-masking substance having a molecular weight higher than about 2,000 in high concentration in a volatile solvent to be used for dissolving or suspending midecamycin as a bitter pharmaceutical ingredient, adding the midecamycin to the resulting solution followed by kneading, adding silicic acid anhydride to the resulting kneaded substance to form a powder and granulating said powder using a solution of the ethyl cellulose in a fluidized bed granulator, said volatile solvent not exerting a degrading effect upon said ethyl cellulose or upon said midecamycin, the amount of said ethyl cellulose to be dissolved in said solvent being about 0.5 to about three times the amount of said midecamycin and the amount of said ethyl cellulose used for said granulation being about 1/10 to about 1/5 the amount thereof used for said dissolving.

2. A process for preparing granular preparations for oral administration having no bitter taste which comprises dissolving or suspending midecamycin as a bitter pharmaceutical ingredient in high concentration in a volatile solvent for dissolving a pharmaceutically acceptable, water insoluble ethyl cellulose as a bitter taste-masking substance having a molecular weight higher than about 2,000, adding the ethyl cellulose to the resulting solution or suspension followed by kneading, adding silicic acid anhydride to the resulting kneaded substance to form a powder and granulating said powder using a solution of said ethyl cellulose in a fluidized bed granulator, said volatile solvent not exerting a degrading effect upon said ethyl cellulose or upon said midecamycin, the amount of said ethyl cellulose added to said solution or said suspension being about 0.5 to about three times the amount of said midecamycin and the amount of said ethyl cellulose used for said granulation being about 1/10 to 1/5 the amount used for said addition.

3. The process according to claim 1, wherein the amount of said ethyl cellulose is dissolved in an amount of 0.5 to 2 times the amount of the midecamycin.

4. The process according to claim 2, wherein said ethyl cellulose is added to said solution or suspension in an amount of 0.5 to 2.0 times the amount of said midecamycin.

* * * * *